US007235683B2

(12) United States Patent
Janeiro et al.

(10) Patent No.: US 7,235,683 B2
(45) Date of Patent: Jun. 26, 2007

(54) ORGANOCHLOROSILANE AND DIPODAL SILANE COMPOUNDS

(75) Inventors: Benigno A. Janeiro, Burlington, NJ (US); Barry C. Arkles, Dresher, PA (US)

(73) Assignee: Gelest Inc., Morrisville, PA (US)

( * ) Notice: Subject to any disclaimer, the term of this patent is extended or adjusted under 35 U.S.C. 154(b) by 0 days.

(21) Appl. No.: 11/554,743

(22) Filed: Oct. 31, 2006

(65) Prior Publication Data

US 2007/0060765 A1 Mar. 15, 2007

Related U.S. Application Data

(62) Division of application No. 10/856,194, filed on May 28, 2004.

(60) Provisional application No. 60/474,440, filed on May 30, 2003.

(51) Int. Cl.
*C07F 7/04* (2006.01)
*C07F 7/08* (2006.01)
(52) U.S. Cl. ...................... 556/482; 556/487
(58) Field of Classification Search ............... 556/482, 556/487
See application file for complete search history.

(56) References Cited

U.S. PATENT DOCUMENTS 4,613,491 A 9/1986 Jung et al.
6,251,057 B1 6/2001 Jung et al.
6,392,077 B1 5/2002 Jung et al.

OTHER PUBLICATIONS

Kang et al., "Phosphonium Chloride-Catalyzed Dehydrochlorinative Coupling Reactions of Alkyl Halides with Hydridochlorosilanes", *Organometallics*, 22:529-534 (2003).
Benkeser et al., "Silylation of Organic Halides. A New Method of Forming the Carbon-Silcon Bond", *Journal of American Chemical Society*, 91:13, p. 3666 (Jun. 18, 1969).
Furuya et al., "The Condensation Reaction of Trichlorosilane with Allylic Chlorides Catalyzed by Copper Salts in the Presence of a Tertiary Amine", *Journal of Organometallic Chemistry*, 96:C1-C3 (1975).
Corriu et al., "Synthesis and reactivity of bis(triethoxysilyl)methane, tris(triethoxysilyl)methane and some derivatives", Journal of Organometallic chemistry 562:79-88, (1998).

*Primary Examiner*—Samuel Barts
(74) *Attorney, Agent, or Firm*—Akin Gump Strauss Hauer & Feld LLP

(57) ABSTRACT

Processes are provided for producing organchlorosilanes and dipodal silanes in which an organic halide or alkene or chloralkene is reacted with a hydridochlorosilane in the presence of a quaternary phosphonium salt catalyst by providing sufficient heat to effect a dehydrohalogenative coupling reaction and/or a hydrosilylation reaction and venting the reaction to control reaction pressure and to remove gaseous byproducts from the reaction. The processes are preferably continuous using a catalyst in fluid form at reaction pressures not exceeding about 600 psi. The reactions may be carried out substantially isothermally and/or isobarically, for example in a plug flow reactor or continuous stirred tank reactor. The processes may produce novel silylated compounds including 1,2-bis(trichlorosilyl)decane or 1,2-bis(trimethoxysilyl)decane.

2 Claims, 2 Drawing Sheets

ORGANOCHLOROSILANE AND DIPODAL SILANE COMPOUNDS

CROSS-REFERENCE TO RELATED APPLICATIONS

This application is a divisional of U.S. application Ser. No. 10/856,194, filed May 28, 2004, now allowed, which claims the benefit of U.S. provisional patent application 60/474,440, filed May 30, 2003, the disclosures of which are incorporated herein by reference.

BACKGROUND OF THE INVENTION

This invention relates to processes, including continuous processes, for the production of silylated derivative compounds of organic halides and alkenes, including organochlorosilanes and dipodal silanes, useful in a variety of applications including as coupling agents and as surface modifiers of substrates related particularly to water repellency and diagnostic applications.

It has been reported in U.S. Pat. No. 6,392,077 of Jung, et al. that organochlorosilanes can be prepared in a batch process by a dehydrohalogenative coupling reaction of an alkyl halide with a hydrido functional chlorosilane in the presence of a solid phosphonium catalyst or solid supported catalyst, as further described in U.S. Pat. No. 4,613,491 of Jung, et al.

In a similar manner, dipodal silanes are produced either in a two step process in which the dehydrohalogenative coupling reaction of an alkene with a chlorosilane occurs, first immediately followed by a hydrosilylation reaction or in two hydrosilylation steps. However, this reaction also requires the use of a solid catalyst or solid supported catalyst. This process also requires charging a solid catalyst to a batch reactor and, once the reaction is complete, removing the catalyst from the reaction mixture either by filtration or distillation. On a commercial scale, this is a labor- and time-consuming operation.

The reactions reported by Jung are carried out in sealed tube reactors at estimated pressures that exceed 1000 p.s.i. The use of sealed tube reactors also causes redistribution of initial by-products of the reaction resulting in such hazardous materials as dichlorosilane and silane.

Prior to the present invention, the reaction of alkyl halides and hydridochlorosilanes was commercially carried out by a batch process, which included a dehydrochlorinative coupling reaction in the presence of an amine base acceptor and sometimes a copper catalyst (Benkesser et al, *J. Am. Chem. Soc.*, 91 (13):3666–67 (1969); Furuya et al, *J. Organomet. Chem.*, 96: C1–C3 (1975); Corriu et al., *J. Organometal. Chem.*, 562:79–88 (1998)). This is a cumbersome process which requires reacting a chlorosilane with a stoichiometric amount of an amine, which generates a considerable amount of waste by-products. This process also generates amine hydrochloride salts which must be removed by filtration. Amine hydrochloride salts are difficult to filter and are often soluble in the product. As a result, further filtration after product purification is required, and still the amine hydrochloride salts continue to drop out of solution after the products have been standing for extended periods of time.

Thus, the large scale production of organochlorosilanes and dipodal silanes by the above mentioned batch process is cumbersome, expensive and, in the case of the Benkesser process, generates excessive waste, such as amine hydrochloride salts and, in the Jung process, is subject to significant by-product generation, attributed to prolonged exposure to the catalyst at elevated temperatures and pressures resulting in the formation of by-products, such as dichlorosilane and silane gas which are difficult to handle and pyrophoric.

BRIEF SUMMARY OF THE INVENTION

To solve the shortcomings described in the prior art for producing organochlorosilanes, dipodal silanes and other silylated compounds, the present invention provides processes, including continuous type processes, which comprise reacting a hydridochlorosilane compound with either an organic halide or an alkene in the presence of a quaternary phosphonium salt catalyst, preferably in fluid form, resulting in more efficient processes that overcome many of the shortcomings associated with known processes for producing the same or similar compounds.

According to a first process of the present invention, organochlorosilanes are produced by mixing a hydridochlorosilane, an organic halide and a quaternary phosphonium salt catalyst, providing sufficient heat to effect a dehydrohalogenative coupling reaction of the hydridochlorosilane with the organic halide, and venting the reaction to control reaction pressure and to remove gaseous byproducts from the reaction.

According to a second process of the present invention, dipodal silanes are produced by mixing a hydridochlorosilane, an alkene and a quaternary phosphonium salt catalyst, providing sufficient heat to effect a double hydrosilylation reaction of the alkene with the hydridochlorosilane, and venting the reaction to control reaction pressure and to remove gaseous by products from the reaction.

Although the processes of the invention could be carried out as batch reactions, it is preferred and a particular advantage of the processes of the invention that they be carried out continuously for maximum throughput of the reactants and ease of scalability of the reactions to commercial processes. Suitable reactors for carrying out the continuous processes include plug flow reactors and continuous stirred tank reactors.

The catalyst is preferably in fluid form for ease of introducing the catalyst into the reaction system and maintaining contact with the reactants. The fluid form may include, for example, a homogeneous solution, a liquid catalyst, a molten catalyst, or even possibly a slurry of finely divided catalyst powder. Alkyl phosphonium chlorides are the preferred catalysts.

The processes are preferably carried out substantially isothermally, i.e., at constant temperature, and substantially isobarically, i.e., at constant pressure. Moreover, the processes are carried out at relatively low pressures, namely less than 1,000 p.s.i., and preferably not greater than about 600 p.s.i.

In order to produce good product yields, it is important to keep the residence time of the reactants in the reaction zone short. In the case of producing organochlorosilanes, the residence time in a reactor should preferably be not greater than about two hours, in order to keep undesirable byproduct formation to a minimum. In the case of producing dipodal silanes, the residence time in the reactor should preferably not be greater than about five hours, for the same reasons.

The processes of the present invention provide a viable access to new building blocks for various silylated materials, for example, by providing a simple, commercially scalable process for making alkyl silanes which can be converted to further products. In the case of dipodal silanes, the second process of the present invention provides a commercially scalable process for producing bis (chlorosilyl) derivatives, for which no other commercially satisfactory process is presently available.

The invention also provides novel silyl derivatives, namely 1,2-bis(trichlorosilyl)decane and 1,2-bis(trimethoxysilyl)decane, and methods of making the same.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
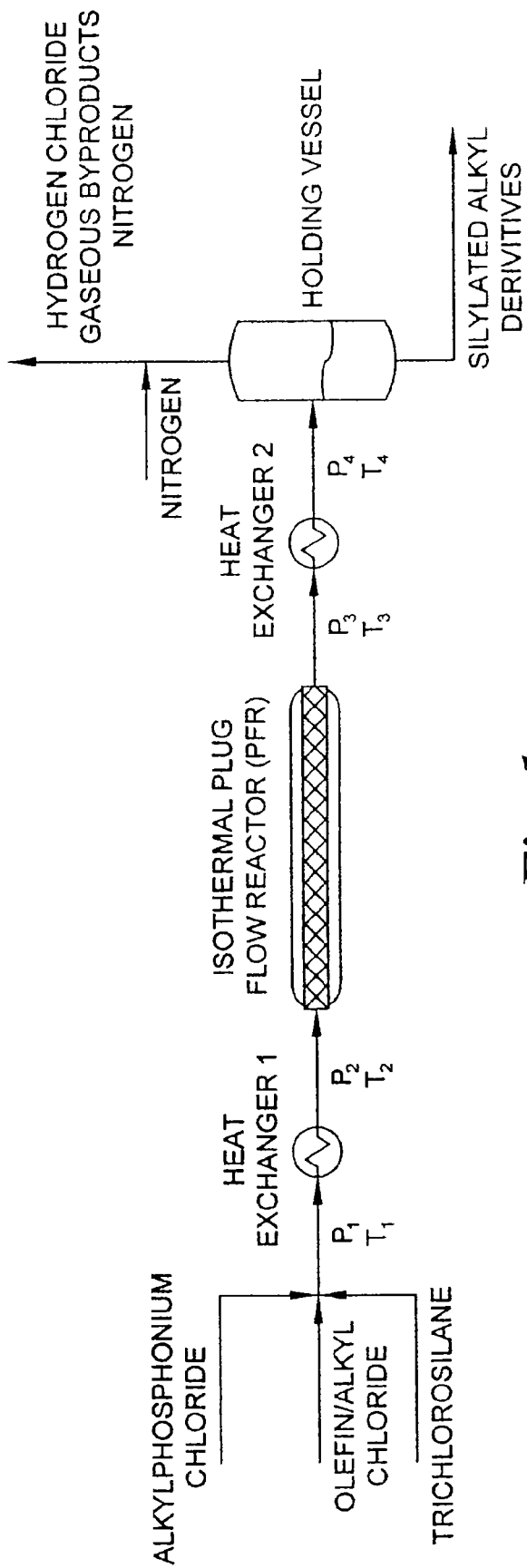
FIG. 1 is a simplified flow diagram of a continuous process for preparing silylated alkyl derivative compounds utilizing a continuous plug flow reactor (PFR) in accordance with a first embodiment of the invention.

The present invention relates to processes, including continuous processes, for the production of silylated derivative compounds of organic halides and alkenes, including organochlorosilanes and dipodal silanes, useful in a variety of applications including as coupling agents and as surface modifiers of substrates related to water repellency and diagnostic applications. More specifically, this invention includes processes in which a quaternary phosphonium salt catalyst, preferably an alkyl phosphonium chloride catalyst, is used, preferably in fluid form, such as dissolved in a solvent, and combined with a hydridochlorosilane and either an alkyl halide or an alkene to form silylated derivative compounds.

Various types of reactors are within the scope of the invention, including continuous plug flow reactors and continuous stirred tank reactors, such that the processes have relatively short residence times and minimal side reactions. The reactor's pressure is dictated by the vapor pressure of the reactants at the reaction temperature. Gaseous by-products, including hydrogen, hydrogen chloride, tetrachlorosilanes, and dichlorosilanes, are allowed to vent in order to control reaction pressure and preferably maintain a constant reaction pressure.

A particular advantage of the present invention is that it provides a continuous process for the dehydrohalogenative coupling reaction of hydrido functional chlorosilanes with alkyl halides and alkenes in the presence of a homogeneous phosphonium catalyst solution. The invention also allows the production of dipodal silanes by the double hydrosilylation of alkenes, preferably to produce vicinal disilyl derivatives.

Still further, the invention allows the production of silane products at relatively low or moderate pressures, for example less than 1000 p.s.i. In so doing, this invention controls the exposure of reactants to catalyst at elevated temperatures and minimizes or eliminates by-product formation.

The processes of the present invention provide greater flexibility in producing organochlorosilanes and dipodal silanes, using relatively short residence times, reducing the amount of waste generated, and allowing recycle of the catalyst. This in turn provides a process with improved process economics on a commercial scale. As a result, this invention provides the ability to produce organochlorosilanes and dipodal silanes on a continuous basis by processes which are more efficient than those of the prior art.

Particularly preferred is the use of the processes of this invention to produce 1,2-disilyl derivatives of alkenes which have utility as coupling agents and as surface modifiers of substrates for water repellency and in diagnostic applications.

Stated otherwise, the present invention relates to processes, including continuous processes, for preparing silyl and disilyl derivative compounds of organic halides and alkenes, including organochlorosilanes and dipodal silanes, wherein the processes comprise a dehydrohalogenative coupling of hydridochlorosilanes with either the organic halide or the alkene in the presence of a quaternary phosphonium salt catalyst. Where the processes of this invention involve reacting an alkene with a hydridochlorosilane, it is understood that the dehydrohalogenative coupling reaction is followed by a hydrosilylation reaction to produce, silylated derivative compounds, including vicinal disilyl derivative compounds, of the alkene.

Dehydrochlorinative coupling reactions for preparing organochlorosilanes are known in the art, for example from U.S. Pat. No. 6,392,077 of Jung et al and Kang, Seung-Hyun et al, "Phosphonium Chloride-Catalyzed Dehydrochlorinative Coupling Reactions of Alkyl Halides with Hydridosilanes," *Organometallics*, 22:529–534 (2003), the disclosures of which are incorporated herein by reference. The processes of the present invention can use virtually any of the hydridochlorosilanes (also known as "hydrochlorosilanes") and organic halides to produce virtually any of the organochlorosilanes disclosed by Jung et al and Kang et al in these references, as well as others which will be apparent to those skilled in the art based on the present disclosure.

Examples of dehydrochlorinative coupling reactions and double hydrosilylation reactions are shown below. These and other related reactions may be carried out according to the processes of the present invention.

The Jung Reaction

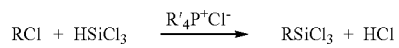

Dehydrochlorinative without base acceptor

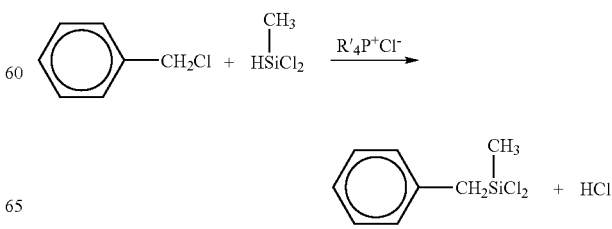

Dehydrochlorinative coupling with Methylhydridosilane

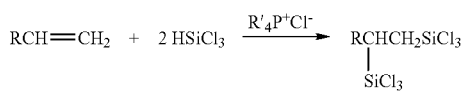

Double Hydrosilylation
Dehyrochlorinative Coupling

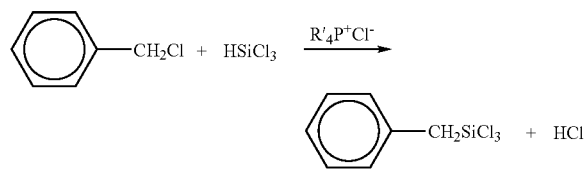

Catalyst: (tetradecyl)tributylphosphonium

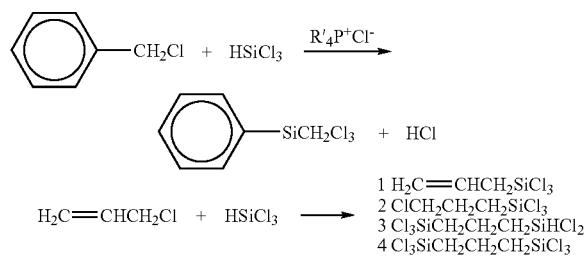

Stirred Autoclave; Catalyst: (tetradecyl)tributylphosphonium Cl

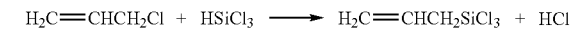

Catalyst: tetrabutylphosphonium chloride/toluene
Double Hydrosilylation

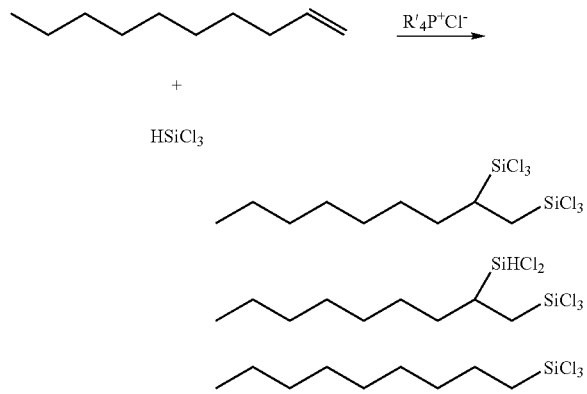

Catalyst: tetradecyltributylphosphonium chloride

The dehydrohalogenative coupling and hydrosilylation reactions described herein are accomplished by heating and mixing the reactants and products in the process as described in more detail below. Preferably, the dehydrohalogenative coupling reactions that occur in the processes of this invention are completed at a rate that maintains no more than a two hour residence time, most preferably the residence time is about one hour, while the hydrosilylation reactions may require up to about four or five hours of residence time. Also, preferably, the reaction is carried out at a temperature from about 100° C. to about 200° C., most preferably from about 120° C. to about 150° C.

Further, while the pressure of the process results from the vapor pressure of the reactants at the reaction temperature, the reaction is maintained at a nearly constant pressure of less than about 1,000 p.s.i. Preferably, the reaction is performed at a pressure of about 50 p.s.i. to about 600 p.s.i., most preferably from about 350 p.s.i. to about 400 p.s.i. It is also preferred that the reactions that result from the processes of this invention take place in an inert atmosphere, preferably nitrogen gas. However, it will be recognized by those of ordinary skill in the art from this disclosure that other inert gases could be used, if desired, without departing from the spirit of the invention.

Preferred in the processes of this invention are alkyl phosphonium chloride catalysts, preferably dissolved in an organic solvent to produce a phosphonium chloride catalyst solution. The phosphonium chloride catalyst used in this invention may be, for example, tetrabutylphosphonium chloride, trihexylbutylphosphonium chloride, (tetradecyl)tributylphosphonium chloride, benzyltributylphosphonium chloride, tetramethylphosphonium chloride, tetraethylphosphonium chloride, benzyltriphenylphosphonium chloride, or ethylene bis(benzyldimethylphosphonium chloride). Preferably, the phosphonium chloride catalyst is an alkyl phosphonium chloride catalyst. Most preferably, the catalyst is selected from the group consisting of tetrabutylphosphonium chloride, trihexylbutylphosphonium chloride, and (tetradecyl)tributylphosphonium chloride. The catalysts described can be dissolved in several different organic solvents including, but not limited to, toluene, diethylbenzene, hexane, tetrahydrofuran, and acetonitrile. However, it will be recognized by those of ordinary skill in the art from this disclosure that other types of solvents, known in the art or to be discovered in the art, could be used, if desired, without departing from the spirit of the invention provided that the solvent is capable of dissolving the selected catalyst and does not adversely affect the reaction.

In a typical preparation, a solid alkyl phosphonium chloride catalyst is dissolved in a suitable solvent, for example toluene, to form a homogeneous solution of liquid or molten alkyl phosphonium chloride catalyst. Preferably, the alkyl phosphonium chloride catalyst, once dissolved, remains in solution. Ultimately, a catalyst which is liquid at process conditions, such as trihexylbutylphosphonium chloride, may be used.

Preferred hydridochlorosilanes for use in the invention include trichlorosilane, methyldichlorosilane and dichlorosilane. Most preferably, the hydridochlorosilane is trichlorosilane. However, it will be recognized by those of ordinary skill in the art from this disclosure that other chlorosilanes could be used, if desired, without departing from the spirit of the invention.

The organic halides may contain an alkyl, allyl or aryl functional group. Exemplary organic halides include, but are not limited to, allyl chloride, allyl bromide, crotyl chloride, benzyl chloride, 1-chlorooctane, 1-chloro-3,3,3-trifluoropropane, (chloromethyl)trichlorosilane, (chloromethyl)dichlorosilane, (chloromethyl)trimethylsilane, (3-chloropropyl)trimethylsilane, 4-fluorobenzyl chloride, 4-chlorobenzyl chloride, 4-methoxybenzyl chloride, 4-phenylbenzyl chloride, 1-chloroethylbenzene, cyclopentylchloride, 2-chlorobutane, isopropyl chloride, dichloromethane, 1,2-dichloroethane, 1,3-dichloropropane, 1-bromo-3-chloropropane, 1,4-dichlorobutane, and 1,4-bis(chloromethyl)benzene. Preferably, the organic halide is either benzyl chloride or allyl chloride.

The alkene may be particularly selected from various olefins or may contain an allyl or aryl functional group. Exemplary alkenes include, but not limited to, ethylene, propylene, 1-butene, 2-butene, isobutylene, 1-pentene, 1-hexene, 1-octene, 1-nonene, 1-decene, 1,2-dichloroethene, 1,2-dibromoethene, 1-bromo-1-chloropropene, 2-bromo-1-chloropropene. Preferably, the alkene is 1-decene.

After the phosphonium chloride catalyst is dissolved in a suitable solvent, the catalyst solution is mixed with a hydridochlorosilane and either an organic halide or an alkene. The amount of hydridochlorosilane used is substantially equivalent to or more than, preferably 2 to 3 times, the amount of organic halide or alkene. The amount of phosphonium chloride catalyst used is sufficient to catalyze the reaction to completion, generally, a 0.02 to 0.1 mole ratio, preferably a 0.05 mole ratio, relative to the amount of organic halide or alkene.

Figure 2:
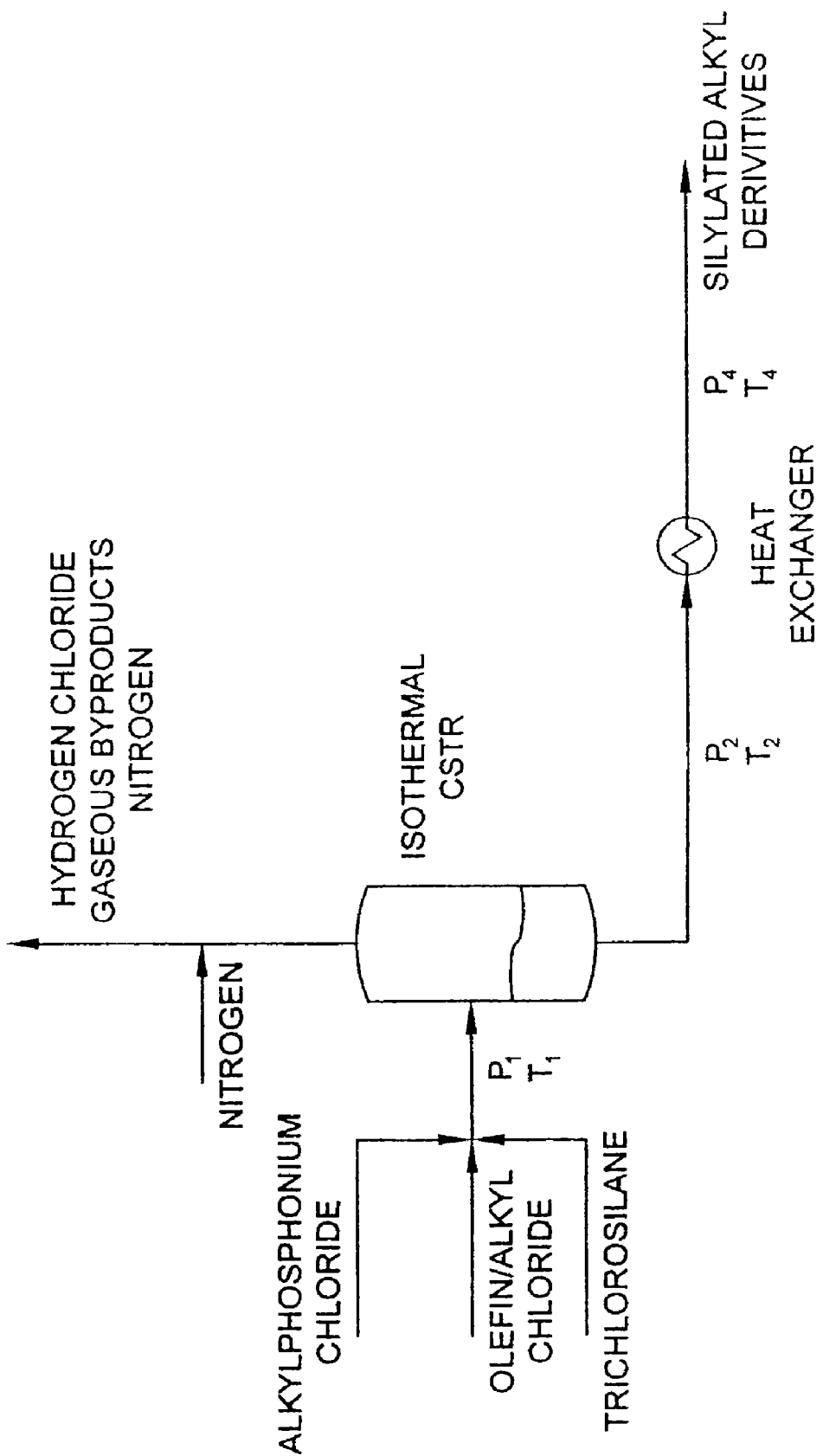
FIG. 2 is a simplified flow diagram of a continuous process for preparing silylated alkyl derivative compounds utilizing a continuous stirred tank reactor (CSTR) in accordance with a second embodiment of the invention.

Referring now to the drawings, there are shown in FIGS. 1 and 2 preferred embodiments of the invention for preparing silylated derivative compounds of organic halides or alkenes (exemplified in FIGS. 1 and 2 as an "olefin"), including organochlorosilane and dipodal silane compounds. More specifically, FIG. 1 shows a continuous process in which an alkylphosphonium chloride catalyst, an olefin or an alkyl chloride, and trichlorosilane are reacted in an isothermal plug flow reactor (PFR) to produce silylated alkyl derivatives of either the olefin or the alkyl chloride.

The process shown in the embodiment of FIG. 1 includes first dissolving the alkylphosphonium chloride catalyst in one of the solvents previously mentioned after which the catalyst solution is combined with the reactants of trichlorosilane and either an alkyl chloride or an alkene. Preferably, the reactants and the catalyst solution are mixed by a static mixer. However, it will be recognized by those of ordinary skill in the art from this disclosure that other types of mixers could be used, if desired, without departing from the spirit of the invention. It will also be recognized by those skilled in the art from the present disclosure that the process can be operated effectively using dual feed pumps (not shown) for feeding the reactants and the catalyst solution to the reactor.

The combination of trichlorosilane, alkyl chloride or alkene, and catalyst solution proceed to a first heat exchanger which increases the temperature of the reactants and catalyst solution from about room temperature to, preferably, about 100° C. to about 200° C.

Referring still to FIG. 1, trichlorosilane, the catalyst solution and the alkyl chloride or alkene enter a continuous reactor which is an isothermal plug flow reactor (PFR). Preferably, the isothermal PFR is a continuous PFR containing more than one heating zone and at least one mixing zone. Most preferably, the isothermal PFR is a continuous isothermal PFR which comprises three heating zones such that Zone 1 heats the reactants and catalyst solution, Zone 2 mixes the reactants and catalyst solution, and Zone 3 cools the reactants and catalyst solution. Also, preferably, Zone 2 comprises a plurality of static mixing elements.

The isothermal PFR is provided with a back pressure regulating valve (not shown) which maintains the process, including the continuous reactor, at the desired constant reaction pressure. Preferably, the pressure in the reactor is maintained between 50 p.s.i. and 600 p.s.i., most preferably from about 350 p.s.i. to about 400 p.s.i., and the temperature in the reactor is maintained at the temperature established by the first heat exchanger which, as previously stated, is preferably about 120° C. to about 200° C.

After passing through the reactor, the reaction products and catalyst solution pass through a second heat exchanger which returns the products to about room temperature before entering a holding vessel. The holding vessel has attached, toward the top of the vessel, a gas discharge pipe which allows by-product and inert gases to vent from the holding vessel thereby assisting the process, including the continuous reactor, to operate at a constant reaction pressure. The gas discharge pipe is connected to an inert gas inlet pipe which provides inert gas, which is preferably nitrogen, to the gas discharge pipe. Inert gas allows the prevention of further undesired reactions in the holding vessel.

The gas discharge pipe is also connected to a scrubber (not shown). The scrubber permits scrubbed gases including, for example, hydrogen and hydrogen chloride, to be safely removed from the process. The scrubber can be of a variety of types and designs including, but not limited to, single or multiple stage types and horizontal or vertical flow design. However, the design of the scrubber should be based on a determination of several factors, including the chemical composition of the by-product gases discharged from the holding vessel. Preferably, the scrubber is an acid gas scrubber.

The holding vessel also has attached, toward the bottom of the vessel, a holding vessel discharge pipe where the reaction products, which are silylated alkyl derivative compounds of the alkene or alkyl chloride, are removed from the process.

Referring now to FIG. 2, a second preferred embodiment of the invention is shown whereby a process is disclosed that is similar to the process described in the first preferred embodiment. The second preferred embodiment, as shown in FIG. 2, is a continuous process in which an alkylphosphonium chloride catalyst, an olefin or an alkyl chloride, and trichlorosilane are reacted in continuous stirred tank reactor (CSTR) to produce silylated alkyl derivatives of either the olefin or the alkyl chloride. The process includes first dissolving the alkylphosphonium chloride catalyst in one of the solvents previously mentioned after which the catalyst solution is combined with the reactants of trichlorosilane and either an alkyl chloride or an alkene. Preferably, the reactants and the catalyst solution are pumped to a mixing vessel (not shown), which is preferably a static mixer. However, as previously stated, it will be recognized by those of ordinary skill in the art from this disclosure that other types of mixers could be used, if desired, without departing from the spirit of the invention. Again, it will also be recognized by those skilled in the art from the present disclosure that the process can be operated effectively using dual feed pumps (not shown) arranged in series or parallel for feeding the reactants and the catalyst solution to the reactor.

The combination of trichlorosilane, alkyl chloride or alkene, and catalyst solution proceed to the CSTR, which is preferably a constant pressure isothermal CSTR, after passing a first pressure gauge and a first temperature gauge, which determines the pressure and temperature of the reactants and catalyst solution. The CSTR increases the temperature of the reactants and catalyst solution from about room temperature to, preferably, about 100° C. to about 200° C.

The CSTR has attached, toward the top of the reactor, a gas discharge pipe which allows by-product and inert gases to vent from the CSTR thereby assisting the process, including the reactor, to operate at a constant reaction pressure. Similar to the first preferred embodiment, the gas discharge pipe is connected to an inert gas inlet pipe which provides inert gas, which is preferably nitrogen, to the gas discharge pipe, for purging and blanketing the holding vessel and diluting potentially pyrophoric byproducts below ignition limits.

The gas discharge pipe is also connected to a scrubber (not shown). The scrubber permits scrubbed gases including, for example, hydrogen chloride and chlorosilanes, to be safely removed from the process. The scrubber can be of a variety of types and designs including, but not limited to, single or multiple stage types and horizontal or vertical flow design. Again, the design of the scrubber should be based on a determination of several factors, including the chemical composition of the by-product gases discharged from the holding vessel. Preferably, the scrubber is an acid gas scrubber.

The CSTR also has attached, toward the bottom of the reactor, a discharge pipe which allows the reaction products, which are silylated alkyl derivative compounds of the alkene or alkyl chloride, and the catalyst solution to discharge to a heat exchanger before being removed from the process. Preferably, the pressure in the CSTR is maintained constant in a range from about 50 p.s.i. to about 600 p.s.i. The heat exchanger returns the reaction products to about room temperature.

It will be recognized by those of ordinary skill in the art from this disclosure that other embodiments of this invention are possible including, for example, arranging a PFR and a CSTR in series, if desired, without departing from the spirit of the invention. It will also be recognized by those of ordinary skill in the art from this disclosure that, where a PFR and a CSTR are arranged in series, piping arrangements and alignments can be such that only one reactor is used while the other is bypassed in order to, for example, repair the bypassed reactor.

The invention will now be described in conjunction with the following specific, non-limiting examples. Unless otherwise stated, all percentages are percentages by weight.

EXAMPLE 1

This example describes a reactor design which is a continuous PFR having three heating zones, such as described above in connection with FIG. 1. More specifically, the heating zones are: Zone 1 which pre-heats the reactants to 180° C.; Zone 2 which has a volume of 2851.7 milliliter equipped with 24 static mixing elements and maintains the reaction mixture at 180° C. for the desired residence time; and Zone 3 which reduces the reaction mixture temperature from the reaction temperature to room temperature. Trichlorosilane, benzyl chloride and a 50% solution of tetradecyltributylphosphonium chloride in toluene are fed to the PFR reactor by a dual feed pump in a 3:1:0.1 molar ratio, respectively, at a rate molar to maintain a one hour residence time in the reactor. The reaction pressure is adjusted by utilizing a back-pressure regulating valve set to 350 p.s.i. The reaction products are collected in a vessel which allows a by-product of hydrogen chloride to be vented to an acid gas scrubber. A gas chromatogram (GC) of the reaction mixture reveals that the mixture is composed of 61.2 weight percent benzyltrichlorosilane and a balance of tetrachlorosilane and toluene.

EXAMPLE 2

By utilizing the same reactor, ancillary equipment and procedure as in Example 1 above, trichlorosilane, 1-decene and tetradecyltributylphosphonium chloride 50% in toluene are fed in a 2:1:0.1 molar ratio, respectively, at a rate to maintain a two hour residence time. As in Example 1, the reaction mixture is maintained at a temperature of 180° C. and a pressure of 350 p.s.i. The reaction mixture is collected in a vessel which allows a by-product of hydrogen chloride to be vented to an acid gas scrubber. A gas chromatogram of the reaction mixture shows that the mixture is 5.4 weight percent decyltrichlorosilane, 70.3 weight percent 1,2-bis(trichlorosilyl)decane (a novel compound), trichlorosilyldichlorosilyldecane isomers, and a balance of tetrachlorosilane and toluene.

EXAMPLE 3

By utilizing the same reactor, ancillary equipment and procedure as Example 1 above, trichlorosilane allyl chloride and tetrabutylphosphonium chloride 50% in toluene are fed in a 2:1:0.05 molar ratio, respectively, at a rate to maintain a one hour resistance time. Zone 2 of the reactor maintains the temperature of the reaction mixture at 130° C., and the pressure in the reactor is adjusted by setting the back-pressure regulated valve to 150 p.s.i. to 200 p.s.i. The reaction mixture is collected in a vessel which allows the hydrogen chloride by-product to be vented to an acid gas scrubber. A gas chromatogram of the reaction mixture shows that the mixture was 48 wt % allyltrichlorosilane, 3 wt % chloropropyltrichlorosilane and 2 wt % 1,3-bis(trichlorosilyl)propane, the balance being composed of tetrachlorosilane and toluene.

EXAMPLE 4

Trichlorosilane, allyl chloride and tetrabutylphosphonium chloride 50% in toluene are fed to a continuous isothermal 5 gallon CSTR of the type shown in FIG. 2 in a 2:1:0.05 molar ratio, respectively, at a rate to maintain a one hour residence time in the reactor. The reactor is operated at a temperature of 130° C., and a back-pressure regulating valve was set at a pressure of 350 p.s.i. to control reaction pressure. A hydrogen chloride gas by-product is continuously vented to an acid gas scrubber, while the liquid phase reaction products are continuously removed from the reactor via a heat exchanger to bring the mixture to room temperature, before being collected in a vessel. A gas chromatogram of the reaction mixture shows that the mixture is 45 weight percent allyltrichlorosilane, 5 weight percent 1,3-bis(trichlorosilyl)propane, 3 weight percent chloropropyltrichlorosilane, and a balance of tetrachlorosilane and toluene.

EXAMPLE 5

This example demonstrates the formation of 1,2-bis(trimethoxysilyl)decane (a novel compound) by reacting a 1,2-bis(trichlorosilyl)decane and 1-trichlorosilyl-2-dichlorosilyldecane mixture, such as obtained in Example 2, with trimethylorthoformate and methyl alcohol, using chloroplatinic acid (catalyst) and tetrahydrofuran in a 3-liter 4 neck flask equipped with a magnetic stirrer, pot thermometer, addition funnel and reflux condenser. The reactor was charged with 936.8 grams of 1,2-bis(trichlorosilyl)decane and 1-trichlorosilyl-2-dichlorosilyldecane mixture and heated to 40° C. Trimethylorthoformate was added to the flask at a rate to control the evolution of methyl chloride. The reaction mixture was heated to 150° C. and then allowed to cool to 80° C., at which point 160.2 milliliters of methyl alcohol and 1 milliliter of 5 percent chloroplatinic acid dissolved in tetrahydrofuran were added to the reactor flask and heated to 120° C. for 2 hours. The reaction mixture was distilled and yielded 624 grams of 1,2-bis(trimethoxysilyl) decane having a boiling point of 132° C. at 0.4 millimeters Hg, a density of 0.984 at 20° C., and a refractive index of 1.4303 at 20° C.

While Examples 1–4 above demonstrate continuous processes according to the invention, the following Examples 6–11 are batch processes, which nevertheless demonstrate the potential for commercial scalability with the processes of the invention.

EXAMPLE 6

A 1 liter high pressure reactor equipped with overhead stirring, an adjustable pressure relief valve and a thermowell was charged with 126.4 grams of 1-decene, 370 grams of trichlorosilane and 58.6 grams of a 50 weight percent tetrabutylphosphonium chloride in toluene solution. The pressure relief valve was set to vent at 350 p.s.i., and the reaction mixture was heated to 200° C. for a period of 5 hours. A gas chromatogram which revealed that the reaction products were primarily composed of 5.4 weight percent decyltrichlorosilane and 70.3 weight percent of 1,2-bis(trichlorosilyl)decane, which is a novel compound.

EXAMPLE 7

A 1 liter high pressure reactor equipped with overhead stirring, an adjustable pressure relief valve and a thermowell was charged with 126.4 grams of 1-decene, 370 grams of trichlorosilane and 28 grams of (tetradecyl)tributylphosphonium chloride. The pressure relief valve was set to vent at 600 p.s.i., and the reaction mixture was heated to 200° C. for a period of 6 hours. It was observed that a positive pressure in the reactor was not generated until the reaction temperature reached about 195° C. A gas chromatogram revealed that the reaction products were primarily composed of 13.2 weight percent decyltrichlorosilane and 57 weight percent 1,2-bis(trichlorosilyl)decane.

The above reaction was repeated at different parameters as indicated below with the corresponding conversions and yields shown.

| Pressure (atm) | Temp (° C.) | Time (hr) | $HSiCl_3:C_{10}H_{20}$ | Conversion (%) | $RSiCl_3$ (%) | $R(SiCl_3)(SIHCl_2)$ (%) | $R(SiCl_3)_2$ (%) |
|---|---|---|---|---|---|---|---|
| 43.3 | 180 | 1 | 3:1 | >99 | 18.3 | 2.5 | 79.2 |
| 23.3 | 200 | 5 | 3:1 | 91.6 | 7.2 | 5.7 | 87.1 |
| 23.3 | 200 | 4 | 4:1 | 96.3 | 25.2 | 5.4 | 68.5 |

EXAMPLE 8

A 1 liter high pressure reactor equipped with overhead stirring, an adjustable pressure relief valve and a thermowell was charged with 115.3 grams of benzyl chloride, 370 grams of trichlorosilane and 27 grams of (tetradecyl)tributylphosphonium chloride dissolved in 56 grams of toluene. The pressure relief valve was set to vent at 350 p.s.i., and the reaction mixture was heated to 150° C. for a period of 1 hour. A gas chromatogram revealed that the reaction products contained 35.9 weight percent benzyltrichlorosilane.

EXAMPLE 9

A 1 liter high pressure reactor equipped with overhead stirring, an adjustable pressure relief valve and a thermowell was charged with 148.2 grams of allyl chloride, 524.7 grams of trichlorosilane and 57.1 grams of a 50 weight percent (tetradecyl)tributylphosphonium chloride in toluene solution. The pressure relief valve was set to vent at 400 p.s.i. and the reaction mixture was heated to 130° C. for a period of 2 hours. A gas chromatogram revealed that the reaction mixture was composed of 48 weight percent allyltrichlorosilane and 1.5 weight percent of 1,3-bis(trichlorosilyl)propane.

EXAMPLE 10

A 1 liter high pressure reactor equipped with overhead stirring, an adjustable pressure relief valve and a thermowell was charged with 148.2 grams of allyl chloride, 524.7grams of trichlorosilane and 114.2 grams of a 50 weight percent (tetradecyl)tributylphosphonium chloride in toluene solution. The pressure relief valve was set to vent at 400 p.s.i., and the reaction mixture was heated to 130° C. for a period of 2 hours. A gas chromatogram revealed that the reaction mixture was composed of 3 weight percent allyltrichlorosilane and 15 weight percent of 1,3-bis(trichlorosilyl)propane.

EXAMPLE 11

A 1-gallon reactor, equipped with a pressure relief valve, was charged with 807.2 grams of chloromethyltrichlorosilane, 1,185.0 grams of trichlorosilane and 129 grams of trihexyltetradecylphosphonium chloride. The pressure relief valve was set to 650 psi and the reaction mixture was heated to 150° C. Once the reaction mixture reached 50° C., an exothermic reaction initiated and caused a very rapid temperature rise as well as pressure. The reaction temperature peaked at 240° C. in approximately 15 minutes with continuous venting of hydrogen chloride at 650 psi. Once the exothermic reaction was complete, the reaction mixture was allowed to cool to 150° C. and held at that temperature for 3 hours; the pressure remained constant at 250 psi. The reaction mixture was cooled to room temperature and 1,742 grams were discharged from the reactor. A gas chromatogram of the reaction mixture showed that it was composed of 40.74 wt % bis(trichlorosilyl)methane.

COMPARATIVE EXAMPLE

A 22-liter reaction flask equipped with overhead mechanical stirring, a pot thermometer, a reflux condenser, an addition funnel and nitrogen overgas was charged with 831 grams of toluene and 2751.5 grams of triisopropylamine. In a separate container, 2430.6 grams of benzyl chloride and 3120.4 grams of trichlorosilane were mixed in a container and then added to the reaction mixture at a rate to maintain a reaction temperature below reflux. Once the benzyl chloride and trichlorosilane addition was complete, the mixture was heated to reflux for 24 hours after which a gas chromatograph analysis was conducted to confirm that the reaction was complete. The reaction mixture was then permitted to cool to room temperature after which it was subjected to filtration. The filter cake was washed several times with hexane and resulted in a total of 5050 grams of wet amine hydrochloride salts. The filtrate was then distilled yielding 2382 grams of benzyl trichlorosilane which appeared hazy. As a result of its hazy appearance, it was concluded that the distillation product required additional filtration, i.e., the haze indicates the presence of a large number of byproducts, which are difficult to separate and adversely affect the yield for this conventional technology.

The processes of the invention produce silyl and disilyl derivative compounds, including organochlorosilanes and dipodal silanes, including particularly vicinal disilyl derivatives, such as 1,2-disilyl derivative compounds in high yield. The mixture of compounds produced from the processes of this invention and the yield will vary and are based on several factors, including the compositions of the reactants and catalyst, as well as the operating conditions, such as process residence time, temperature and pressure.

It is an object of this invention to provide continuous processes for manufacturing silyl and disilyl derivative compounds of organic halides and alkenes in a manner that ensures product formation and minimizes by-product formation, thereby resulting in more efficient processes compared to those in the prior art. This is accomplished, by designing the processes as described herein and as shown in the drawings such that there exists controlled exposure of reactants to the catalyst solution at elevated temperatures and operating pressures.

The products prepared from the processes of this invention have significant commercial potential. However, the known uses of silanes and silane derivative compounds produced from less efficient batch processes have been documented and therefore are established. For example, it is known that 1,2-disilyl derivatives, which are also products of the processes of this invention, are useful as coupling agents and for modifying the surface of substrates related to water repellency and diagnostic applications. This invention provides efficient and improved processes for producing silyl and disilyl derivative compounds for existing, and possibly new, products. Examples of such products are illustrated in below:

Silane Coupling Agents

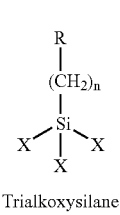
Trialkoxysilane

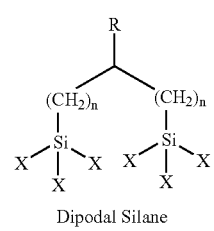
Dipodal Silane

Dipodal Silanes

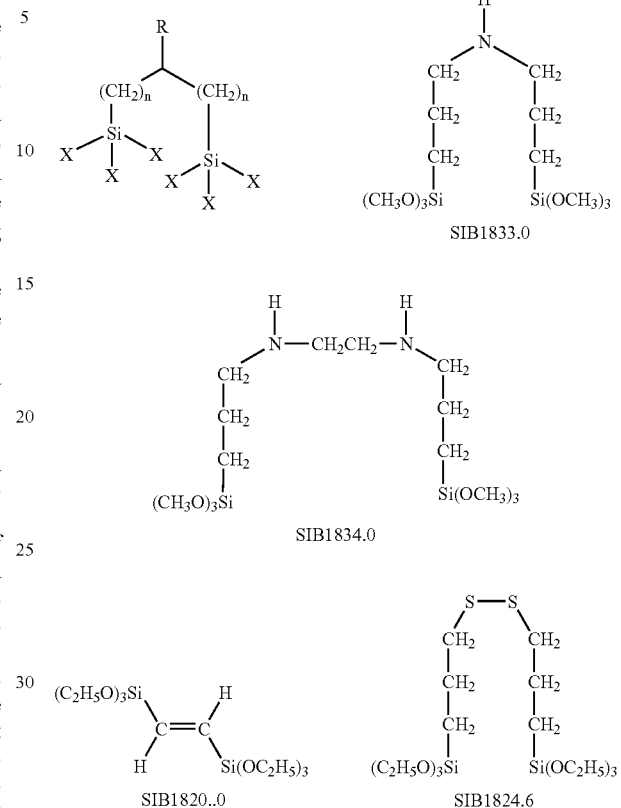

Dipodal tetrasulfide silanes are used in "green" tires, for example.

Terminal Dipodal Silanes

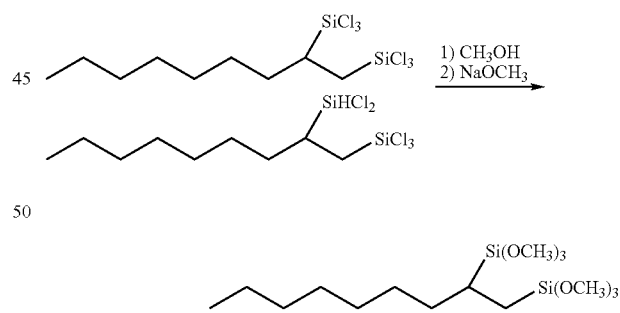

Non-Functional Dipodals

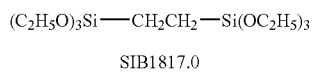

SIB1817.0

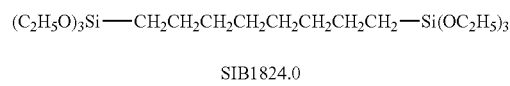

SIB1824.0

-continued

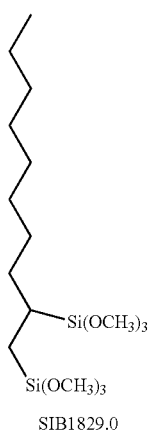

SIB1829.0

-continued

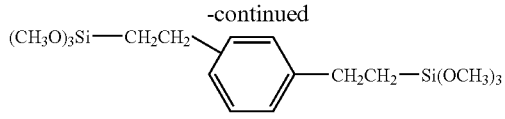

SIB1831.0

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. The compound 1,2-bis(trichlorosilyl)decane.
2. The compound 1,2-bis(trimethoxysilyl)decane.

* * * * *